(12) United States Patent
Ogushi et al.

(10) Patent No.: US 11,617,407 B2
(45) Date of Patent: Apr. 4, 2023

(54) HELMET AND SENSOR ATTACHMENT STRUCTURE

(71) Applicant: Murata Manufacturing Co., Ltd., Kyoto (JP)

(72) Inventors: Naoki Ogushi, Kyoto (JP); Tsuyoshi Yamashita, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 330 days.

(21) Appl. No.: 16/997,015

(22) Filed: Aug. 19, 2020

(65) Prior Publication Data
US 2020/0375295 A1 Dec. 3, 2020

Related U.S. Application Data

(63) Continuation of application No. PCT/JP2019/017563, filed on Apr. 25, 2019.

(30) Foreign Application Priority Data

May 15, 2018 (JP) .............................. JP2018-093645

(51) Int. Cl.
*A42B 3/04* (2006.01)
*A42B 3/30* (2006.01)
*A61B 5/026* (2006.01)

(52) U.S. Cl.
CPC .............. *A42B 3/0433* (2013.01); *A42B 3/30* (2013.01); *A61B 5/026* (2013.01)

(58) Field of Classification Search
CPC ......... A42B 3/0433; A42B 3/14; A42B 3/142; G08B 25/10; G08B 7/06; A61B 5/01; A61B 5/02
See application file for complete search history.

(56) References Cited

U.S. PATENT DOCUMENTS

2003/0032893 A1 2/2003 Koch
2014/0378853 A1 12/2014 McKinney et al.
(Continued)

FOREIGN PATENT DOCUMENTS

JP 2017197866 A 11/2017
JP 2017214673 A 12/2017
(Continued)

OTHER PUBLICATIONS

International Search Report issued in Application No. PCT/JP2019/017563, dated Jul. 16, 2019.
(Continued)

*Primary Examiner* — Katherine M Moran
(74) *Attorney, Agent, or Firm* — Pearne & Gordon LLP

(57) ABSTRACT

A helmet includes a non-contact sensor for a living body, a cap body, and a headband attached to an inner side of the cap body. The headband is provided with a first projection and a second projection on a surface facing a front head portion (FD) of the cap body. The non-contact sensor for the living body includes a first housing having a first surface and a second surface opposing the first surface, a first claw portion provided on the first surface, and a second claw portion provided on the second surface. The first claw portion is brought into contact with and fixed to the first projection, and the second claw portion is brought into contact with and fixed to the second projection.

18 Claims, 10 Drawing Sheets

(56) References Cited

U.S. PATENT DOCUMENTS

2017/0000417 A1    1/2017  Zhavoronkov et al.
2021/0030097 A1*   2/2021  Morgan ................... A61B 5/01

FOREIGN PATENT DOCUMENTS

JP      2019035161 A    3/2019
KR    1020120083946 A   7/2012

OTHER PUBLICATIONS

Written Opinion issued in Application No. PCT/JP2019/017563, dated Jul. 16, 2019.

* cited by examiner

HELMET AND SENSOR ATTACHMENT STRUCTURE

This is a continuation of International Application No. PCT/JP2019/017563 filed on Apr. 25, 2019 which claims priority from Japanese Patent Application No. 2018-093645 filed on May 15, 2018. The contents of these applications are incorporated herein by reference in their entireties.

BACKGROUND

Technical Field

The present disclosure relates to a helmet and to a structure for attaching a sensor to the helmet.

Various helmets to which sensors are attached have been put into practical use. When a worker wears such a helmet, the sensor measures biological data of the worker in a workplace, environmental data of the workplace, body motion data accompanying a movement of the worker, and the like. Further, an administrator detects whether any abnormal situation has occurred against the worker or in the workplace by comparing the measured data with accumulated data in the past.

Patent Document 1: Japanese Unexamined Patent Application Publication No. 2017-197866

BRIEF SUMMARY

However, a sensor with a structure described in Patent Document 1 acquires biological signals by an electrode of the sensor contacting the forehead of the worker. In other words, the electrode of the sensor is brought into contact with the forehead (skin) of the worker. Because of this, there is a possibility that the worker has an uncomfortable feeling, a possibility that allergic reactions to the metal of the electrode occur depending on the workers, or the like.

The present disclosure provides a helmet provided with a sensor that is able to acquire biological information or environmental information while reducing an uncomfortable feeling of a wearer when wearing the helmet.

A helmet according to an aspect of the present disclosure includes a non-contact sensor for a living body, a cap body, and a headband attached to an inner side of the cap body. The headband is provided with a first projection and a second projection on a surface facing a front head portion of the cap body. The non-contact sensor for the living body includes a first housing having a first surface and a second surface opposing the first surface, a first claw portion provided on the first surface, and a second claw portion provided on the second surface. The first claw portion is brought into contact with and fixed to the first projection, and the second claw portion is brought into contact with and fixed to the second projection.

In this configuration, since the sensor does not directly contact the head of the worker when the helmet is worn, the uncomfortable feeling when wearing the helmet can be reduced.

The non-contact sensor for the living body according to an aspect of the present disclosure can further include a third claw portion provided on the first surface and a fourth claw portion provided on the second surface. The headband includes a third projection and a fourth projection. The first claw portion is inserted into and fixed to the first projection. The second claw portion is inserted into and fixed to the second projection. The third claw portion is inserted into and fixed to the third projection. The fourth claw portion is inserted into and fixed to the fourth projection. With the above, the non-contact sensor for the living body is fixed to the headband.

In this configuration, the non-contact sensor for the living body can be more reliably fixed to the headband.

The non-contact sensor for the living body according to an aspect of the present disclosure can further include a fifth claw portion having a first fixing hole and provided between the first claw portion and the third claw portion on the first surface, and a sixth claw portion having a second fixing hole and provided between the second claw portion and the fourth claw portion on the second surface.

In this configuration, the non-contact sensor for the living body can be more reliably fixed by passing a fixing band through the first fixing hole and the second fixing hole.

The non-contact sensor for the living body according to an aspect of the present disclosure can further include a third claw portion provided on the first surface. The headband includes a third projection and a fourth projection. The first claw portion is inserted into and fixed to the first projection. The third claw portion is inserted into and fixed to the third projection. The second claw portion is sandwiched between the second projection and the fourth projection.

In this configuration, the non-contact sensor for the living body can be easily fixed to the headband.

A first fixing hole and a second fixing hole can be formed in the first claw portion and the second claw portion, respectively, of the non-contact sensor for the living body according to an aspect of the present disclosure.

In this configuration, the non-contact sensor for the living body can be more reliably fixed by passing a fixing band through the first fixing hole and the second fixing hole.

The helmet according to an aspect of the present disclosure can include a second housing disposed on an outer side portion of the cap body, and include a power storage unit, a radio communication unit, and an environmental sensor each housed in the second housing. The first housing and the second housing are connected to each other by wiring disposed between the inner side of the cap body and the headband.

In this configuration, the second housing provided with the power storage unit, the radio communication unit, and the environmental sensor can be disposed on the outer side portion of the cap body. This makes it possible to cause the sensor disposed inside the cap body to be miniaturized or thinner, and to reduce the uncomfortable feeling of the worker. Further, by connecting the first housing and the second housing by the wiring, data obtained by a first non-contact sensor can be output to an outside via the radio communication unit in the second housing.

The first housing of the non-contact sensor for the living body according to an aspect of the present disclosure can include the first surface, the second surface, a body portion, and a lid portion. The first surface, the second surface and the body portion, or the first surface, the second surface and the lid portion are bonded to one another by a double-sided tape.

This configuration makes it possible to cause the first non-contact sensor to be miniaturized or thinner.

The non-contact sensor for the living body according to an aspect of the present disclosure can include a sensor element making use of an optical system, and that the headband include a measuring hole. The measuring hole and a light input/output portion of the sensor element face each other.

This configuration makes it possible to acquire sensing signals accurately from the light input/output portion of the sensor element, and to reliably detect living body signals.

A helmet according to an aspect of the present disclosure includes a non-contact sensor for a living body, a cap body, and a headband disposed on an inner side of the cap body. The non-contact sensor for the living body is fixed between the cap body and the headband.

In this configuration, since the sensor does not directly contact the head of the worker when the helmet is worn, the uncomfortable feeling when wearing the helmet can be reduced.

A sensor attachment structure according to an aspect of the present disclosure is an attachment structure configured to attach a non-contact sensor for a living body to a band. The non-contact sensor for the living body includes a body portion that is formed in a rectangular shape and has a first surface and a second surface opposing the first surface, a first claw portion provided on the first surface, and a second claw portion provided on the second surface. The non-contact sensor for the living body is attached by using the first claw portion and the second claw portion.

In this configuration, since the sensor does not directly contact the worker when the sensor is mounted, the uncomfortable feeling when mounting the sensor can be reduced.

According to the present disclosure, it is possible to provide a helmet provided with a sensor able to acquire biological information or environmental information while reducing an uncomfortable feeling of a wearer when wearing the helmet.

DETAILED DESCRIPTION

First Embodiment

Figure 1:
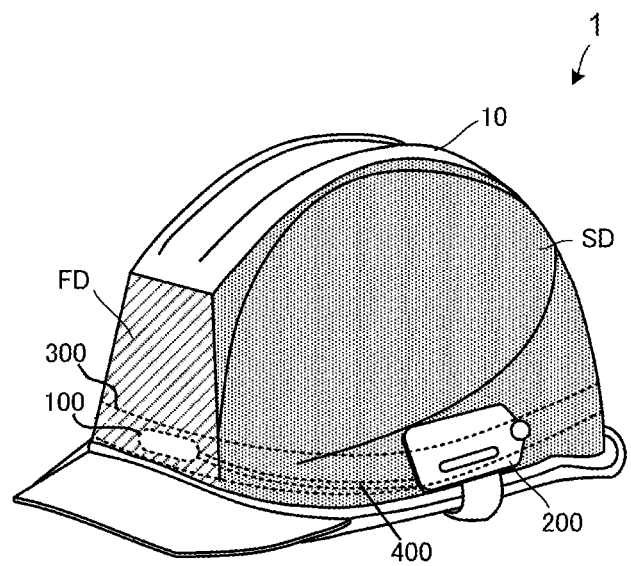
FIG. 1 is an external view (plan view) of a helmet 1 according to a first embodiment of the present disclosure.
Figure 2:
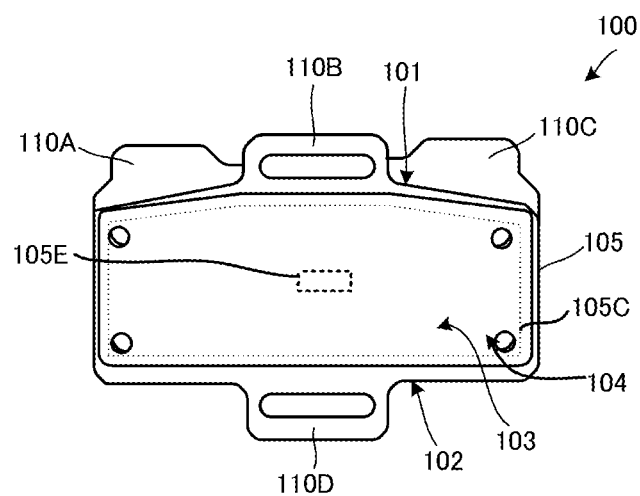
FIG. 2 is an external view of a first sensor module 100 according to the first embodiment of the present disclosure.
Figure 3:
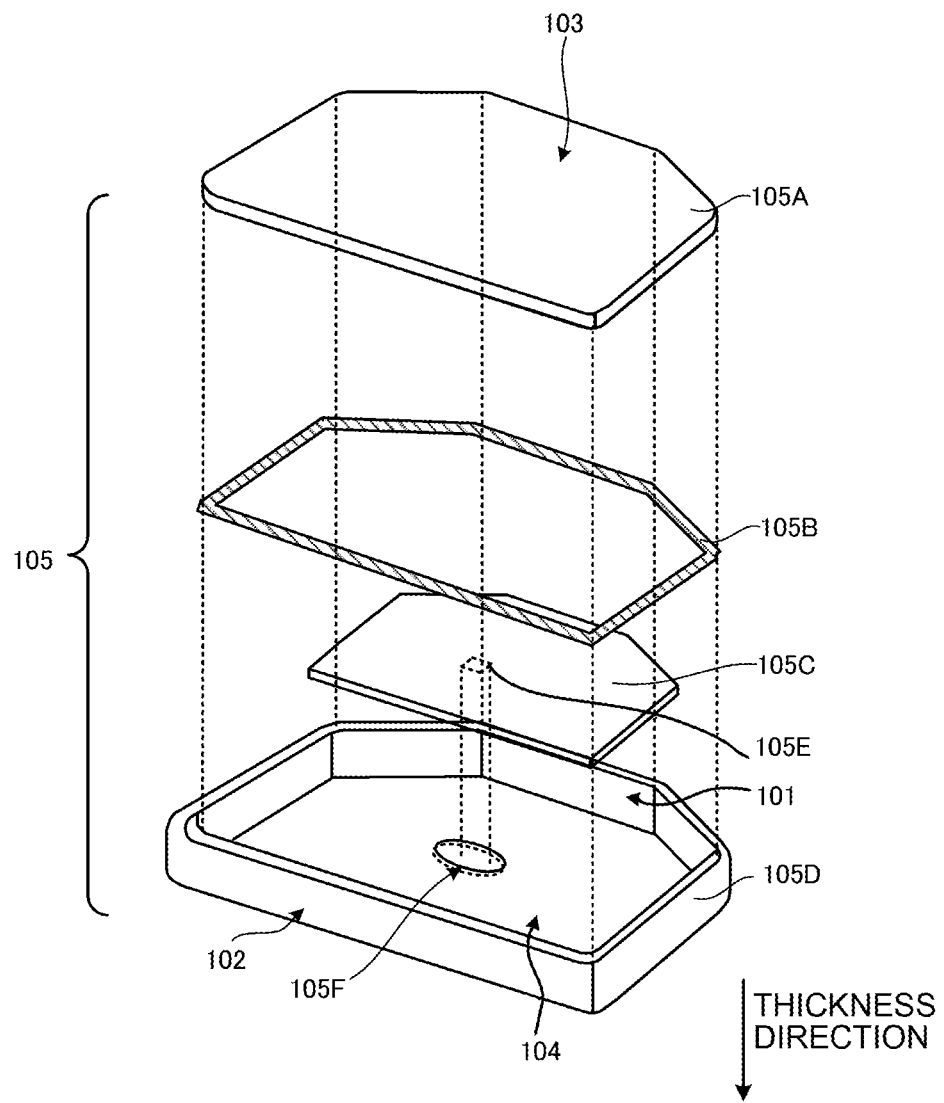
FIG. 3 is an exploded perspective view of the first sensor module 100 according to the first embodiment of the present disclosure.
Figure 4A:
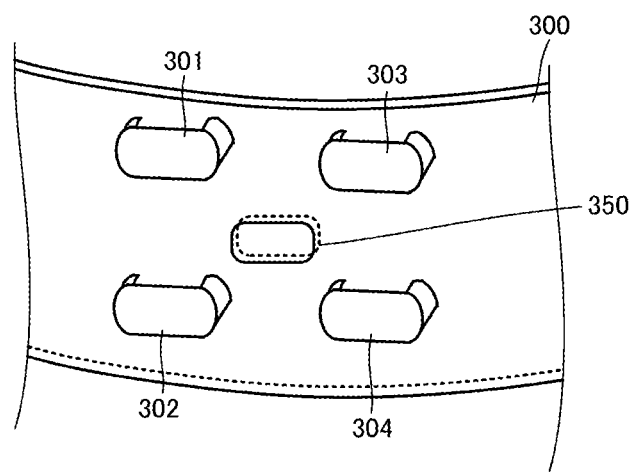
FIG. 4A is an enlarged view illustrating part of a configuration of a headband 300 according to the first embodiment of the present disclosure.
Figure 4B:
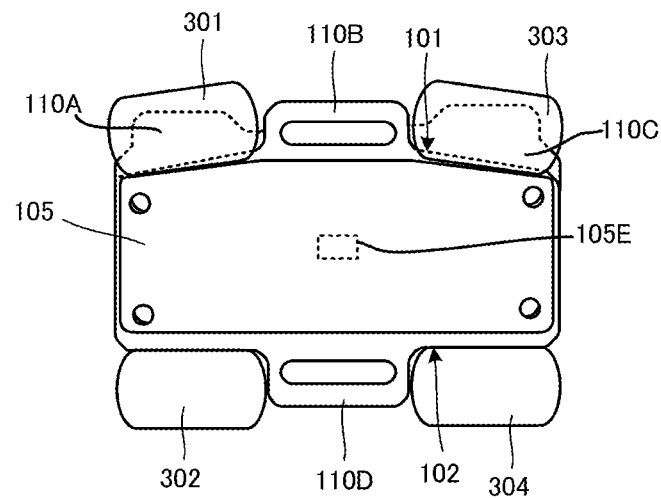
FIG. 4B is a schematic view in which the first sensor module 100 is attached.
Figure 5A:
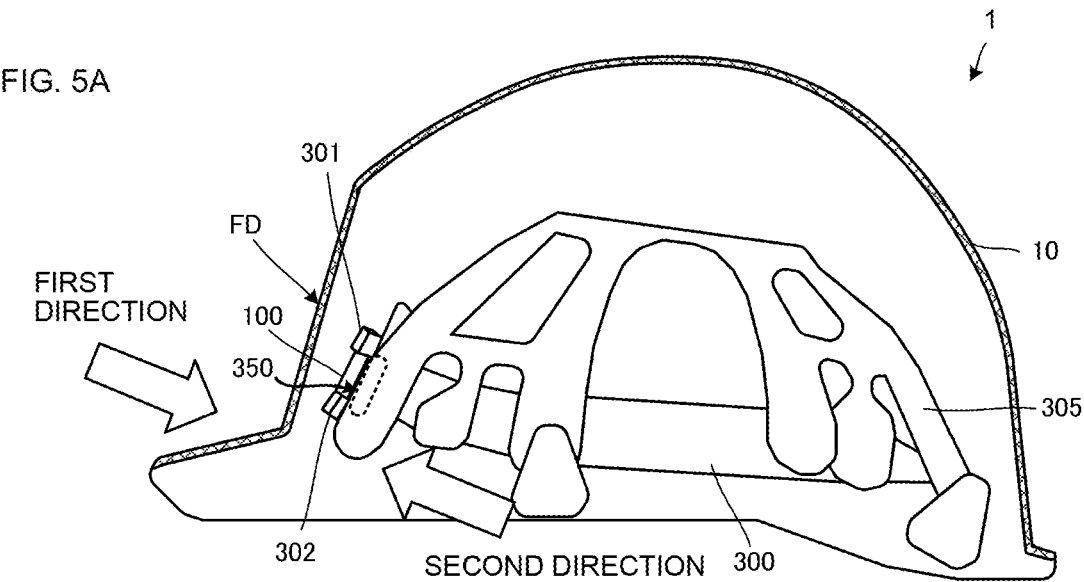
FIG. 5A is a side view illustrating a schematic configuration of the helmet 1 according to the first embodiment of the present disclosure.
Figure 5B:
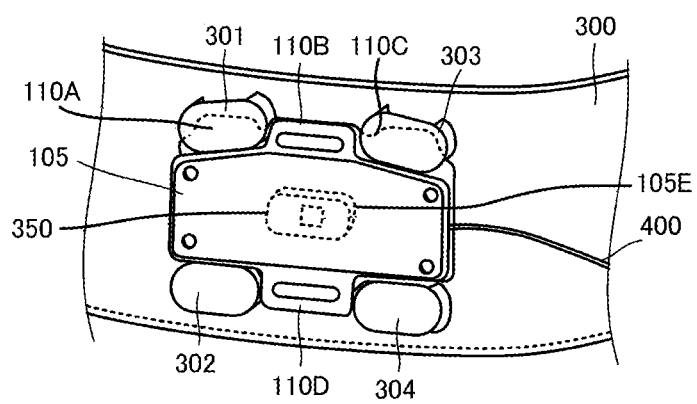
FIG. 5B is a partially enlarged view when a front head portion FD (inside) of the helmet 1 in FIG. 5A is viewed from a first direction.
Figure 5C:
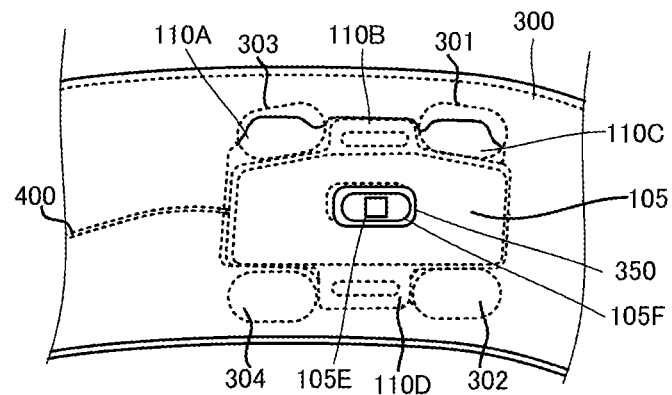
FIG. 5C is a partially enlarged view when the front head portion FD (inside) of the helmet 1 in FIG. 5A is viewed from a second direction.
Figure 6:
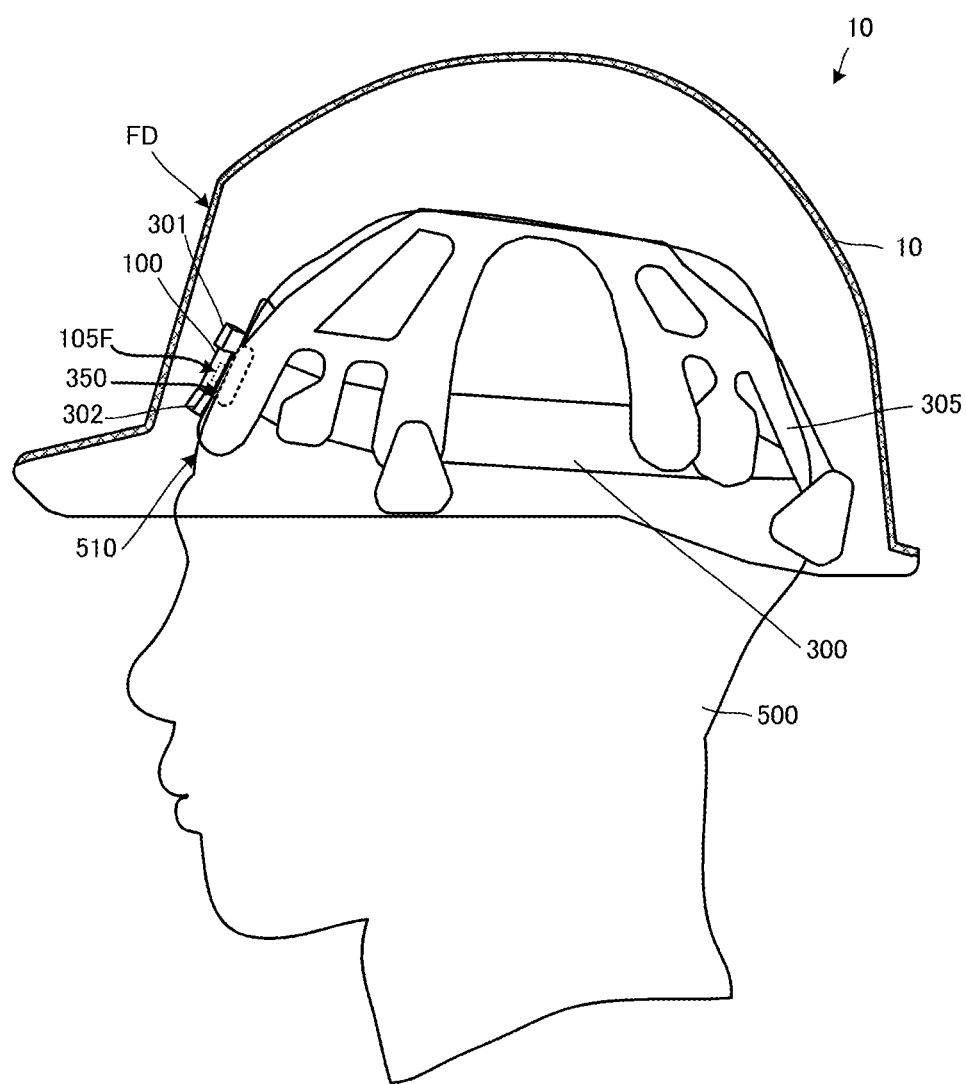
FIG. 6 is a side view in a state in which the helmet 1 according to the first embodiment of the present disclosure is worn.
Figure 7:
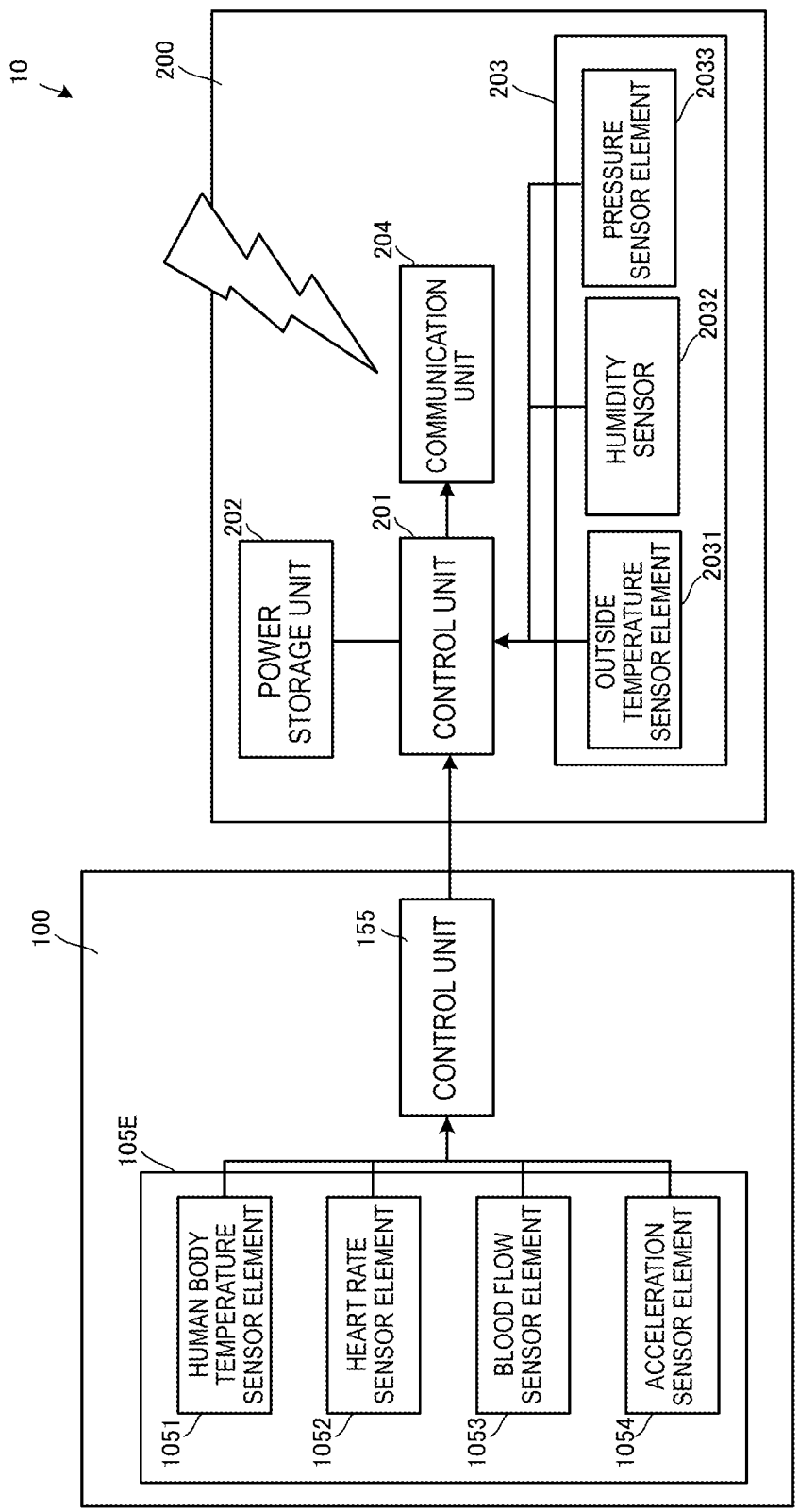
FIG. 7 is a functional block diagram related to the helmet 1 according to the first embodiment of the present disclosure.

An electronic apparatus according to a first embodiment of the present disclosure will be described with reference to the accompanying drawings. FIG. 1 is an external view (plan view) of a helmet 1 according to the first embodiment of the present disclosure. FIG. 2 is an external view of a first sensor module 100 according to the first embodiment of the present disclosure. FIG. 3 is an exploded perspective view of the first sensor module 100 according to the first embodiment of the present disclosure. FIG. 4A is an enlarged view illustrating part of a configuration of a headband 300 according to the first embodiment of the present disclosure, and FIG. 4B is a schematic view in which the first sensor module 100 is attached. FIG. 5A is a side view illustrating a schematic configuration of the helmet 1 according to the first embodiment of the present disclosure, FIG. 5B is a partially enlarged view when a front head portion FD (inside) of the helmet 1 in FIG. 5A is viewed from a first direction, and FIG. 5C is a partially enlarged view when the front head portion FD (inside) of the helmet 1 in FIG. 5A is viewed from a second direction. FIG. 6 is a side view in a state in which the helmet 1 according to the first embodiment of the present disclosure is worn. FIG. 7 is a functional block diagram related to the helmet 1 according to the first embodiment of the present disclosure. In each of the drawings, the dimensional relationship is appropriately changed to make the configuration easy to be seen.

As illustrated in FIG. 1, the helmet 1 includes a cap body 10, a first sensor module 100, a second sensor module 200, a headband 300, and wiring 400.

The helmet 1 is an industrial protective cap (working helmet) that is used in, for example, a construction site, or the like and protects the head of the worker from flying objects and falling objects. The worker wears the helmet 1 (cap body 10) in such a manner that the forehead of the worker is positioned on a side of a front head portion FD.

The headband 300 is a component configured to soften the impact on the helmet 1 (cap body 10) so as to protect the head of the worker. The headband 300 is disposed between the cap body 10 and the worker (head) to wear the helmet 1. The headband 300 has a substantially annular shape with a predetermined width, and extends over the entire circumference of the head including the frontal region, temporal region, and occipital region.

The first sensor module 100 includes a first housing 105, and is fixed to the headband 300. The first sensor module 100 is disposed on the front head portion FD side (the forehead side of the worker) in such a manner as to be sandwiched between the cap body 10 and the headband 300. At this time, the first sensor module 100 is not in contact with the cap body 10 in a stationary state.

The first sensor module 100 is a module that corresponds to a non-contact sensor for a living body of the present disclosure and includes a non-contact sensor element of an optical system. The first sensor module 100 includes, for example, a sensor element for measuring a temperature of the worker wearing the helmet 1 (hereinafter, referred to as the worker), a sensor element for measuring a heart rate of the worker, and the like, and measures biological signals of the worker. With the configuration described above, the first sensor module 100 is disposed at a position close to the forehead of the worker.

The second sensor module 200 includes a second housing, and is fixed to a side head portion SD of the cap body 10. The second sensor module 200 is disposed so as to be in contact with an outside of the cap body 10. The first sensor module 100 and the second sensor module 200 are connected to each other with the wiring 400.

The second sensor module 200 corresponds to an environmental sensor of the present disclosure. The second sensor module 200 includes, for example, a sensor element for measuring an outside temperature, a sensor element for measuring humidity, and the like, and measures a state of an ambient environment of the worker.

The second sensor module 200 includes a radio communication unit to communicate with an external device. By the second sensor module 200 including the radio communication unit, data measured by the first sensor module 100 and data measured by the second sensor module 200 can be output to the external device. Other detailed configurations of the second sensor module 200 will be described later.

A structure of the first sensor module 100 will be described with reference to FIGS. 2 and 3.

First, an external appearance structure of the first sensor module 100 will be described with reference to FIG. 2. The first sensor module 100 includes the first housing 105, a protruding portion 110A, a protruding portion 110B, a protruding portion 110C, and a protruding portion 110D. The first housing 105 includes a first surface 101, a second surface 102, a third surface 103 and a fourth surface 104, and has a substantially rectangular shape in a plan view. The protruding portion 110A, the protruding portion 110B and the protruding portion 110C are formed on the first surface 101 side along a longitudinal direction of the first surface 101, and the protruding portion 110B is formed at a position sandwiched between the protruding portion 110A and the protruding portion 110C. The protruding portion 110D is formed on the second surface 102 side. The protruding portion 110A is a "first claw portion" of the present disclosure, the protruding portion 110D is a "second claw portion" of the present disclosure, and the protruding portion 110C is a "third claw portion" of the present disclosure.

Next, a detailed structure of the first housing 105 in the first sensor module 100 will be described with reference to FIGS. 2 and 3. The first housing 105 includes a lid portion 105A, an adhesive tape 105B, a substrate 105C, a body portion 105D, a sensor 105E, and a light input/output portion 105F. The lid portion 105A has the third surface 103, and the body portion 105D has the first surface 101, the second surface 102, and the fourth surface 104. The sensor 105E is mounted on the substrate 105C.

The body portion 105D has a shape in which vertical planes with respective to all sides of the fourth surface 104 are sequentially connected. In other words, the body portion 105D is formed in a shape like a square vessel. Of these side walls, two side walls opposing each other configure the first surface 101 and the second surface 102. Note that the first surface 101 and the second surface 102 do not need to be disposed in parallel to each other, and it is sufficient that the first surface 101 and the second surface 102 are disposed at positions opposing each other.

The substrate 105C and the sensor 105E are disposed inside the body portion 105D.

The lid portion 105A and the body portion 105D, which configure the first housing 105, are made of resin. That is, it is possible to make the first housing 105 lighter in weight and easier to be processed.

In the first housing 105, the lid portion 105A, the adhesive tape 105B, the substrate 105C, and the body portion 105D are laminated in that order in a thickness direction. The lid portion 105A is bonded to the body portion 105D (first surface 101, second surface 102) with the adhesive tape 105B interposed therebetween.

The adhesive tape 105B is a double-sided tape. It is sufficient that the adhesive tape 105B is made of a material able to bond the lid portion 105A and the body portion 105D. Since the lid portion 105A and the body portion 105D are fixed by the adhesive tape 105B, the thickness of the first housing 105 can be made to be thinner than that in a case of using a screw to fix them.

The light input/output portion 105F is formed in the body portion 105D. More specifically, the light input/output portion 105F is formed at a position facing the sensor 105E formed on the substrate 105C. That is, it is sufficient that the light input/output portion 105F overlaps with the sensor 105E in a plan view of the body portion 105D and has a shape larger in area than at least the sensor 105E.

The first housing 105 may have a structure in which the entire surface thereof is covered with a waterproof sheet or the like. With this, the substrate 105C and the sensor 105E disposed inside the first housing 105 can be protected from moisture, such as sweat of the worker, rain and the like.

A specific structure for fixing the first sensor module 100 (first housing 105) to the headband 300 will be described with reference to FIGS. 4A and 4B. FIG. 4A is an enlarged view of part of the structure of the headband 300. FIG. 4B is a schematic view in which the first sensor module 100 (first housing 105) is fixed to the headband 300.

As illustrated in FIG. 4A, the headband 300 includes a projection 301, a projection 302, a projection 303, and a projection 304. When the locations where the projection 301, the projection 302, the projection 303, and the projection 304 are disposed are connected with a line, a rectangular region is formed. The headband 300 may include a measuring hole 350 passing through the headband 300 in the rectangular region surrounded by the projection 301, the projection 302, the projection 303, and the projection 304. The projection 301 is a "first projection" of the present disclosure, and the projection 302 is a "second projection" of the present disclosure. The projection 303 is a "third projection" of the present disclosure, and the projection 304 is a "fourth projection" of the present disclosure.

The projection 301, the projection 302, the projection 303, and the projection 304 may be shock-absorbing projections provided to reduce the impact received by the cap body 10 of the general helmet (helmet 1).

Next, as illustrated FIG. 4B, a structure in which the first sensor module 100 (first housing 105) is fixed to the headband 300 will be described.

The protruding portion 110A of the first sensor module 100 is inserted into the projection 301 of the headband 300, and the protruding portion 110C of the first sensor module 100 is inserted into the projection 303 of the headband 300. In other words, the protruding portion 110A is in contact with and is fixed to the projection 301, and the protruding portion 110C is in contact with and is fixed to the projection 303. The protruding portion 110D of the first sensor module 100 is disposed so as to be sandwiched between the projection 302 and the projection 304 of the headband 300. In other words, the protruding portion 110D is in contact with and is fixed to the projection 302 and the projection 304. In this manner, the first sensor module 100 (first housing 105) is fixed to the headband 300. In this specification, the phrase "the protruding portion is in contact with and is fixed to the projection" includes a mode in which the protruding portion is inserted into and fixed to the projection, and a mode in which the protruding portion is sandwiched between a plurality of projections.

Since the protruding portion 110B of the first sensor module 100 is disposed so as to be sandwiched between the projection 301 and the projection 303 of the headband 300, the first sensor module 100 (first housing 105) can be more reliably fixed to the headband 300.

Accordingly, a size of the protruding portion 110A may be such that the protruding portion 110A can be inserted into the projection 301 and is unlikely to be detached by vibrations or the like, while a size of the protruding portion 110C may be such that the protruding portion 110C can be inserted into the projection 303 and is unlikely to be detached by vibrations or the like. The protruding portion 110B may be in contact with the projection 301 and the projection 303 in a state of being sandwiched between the projection 301 and the projection 303. A size of the protruding portion 110D may be such that the protruding portion 110D contacts the projection 302 and the projection 304 in a state of being sandwiched between the projection 302 and the projection 304.

The measuring hole 350 is formed in a location facing the sensor 105E of the first sensor module 100. This allows the sensor 105E to accurately measure biological signals of the worker.

Next, a specific configuration of fixing the first sensor module 100 to the helmet 1 will be described with reference to FIGS. 5A, 5B, and 5C.

FIG. 5A is a view illustrating an internal structure of the cap body 10, where part of the cap body 10 is removed and the helmet 1 is viewed from the side head portion SD side. The headband 300 includes an attachment unit 305. The headband 300 is fixed to the cap body 10 via the attachment unit 305. The first sensor module 100 is fixed between the inner side of the cap body 10 and the headband 300.

As illustrated in FIGS. 5B and 5C, similarly to FIGS. 4A and 4B described above, the protruding portion 110A is inserted into the projection 301, and the protruding portion 110C is inserted into the projection 303. The protruding portion 110D is disposed so as to be sandwiched between the projection 302 and the projection 304. Due to this, the first sensor module 100 (first housing 105) is fixed to the headband 300.

Further, the first sensor module 100 (first housing 105) is connected to the second sensor module 200 (not illustrated) via the wiring 400. The biological signal acquired by the first sensor module 100 is output to the second sensor module 200.

The wiring 400 may be covered with a shrinkable tube. With this, the wiring 400 is protected from moisture, humidity, and the like.

As illustrated in FIG. 5C, when the helmet 1 is viewed in the second direction, the measuring hole 350 and the light input/output portion 105F are configured to face each other, thereby making it possible for the sensor 105E to measure the biological signals.

FIG. 6 is an image view in which a worker 500 wears the helmet 1, and is also a view, similar to FIG. 5A, illustrating an internal configuration of the cap body 10, where part of the cap body 10 is removed and the helmet 1 is viewed from the side head portion SD side.

A forehead 510 of the worker 500 is in contact with the headband 300. The first sensor module 100 (first housing 105) faces the forehead 510 with the headband 300 interposed therebetween. That is, the first sensor module 100 is disposed without necessarily being brought into contact with the forehead 510 of the worker 500. Further, the measuring hole 350 formed in the headband 300 and the light input/output portion 105F formed in the first housing 105 of the first sensor module 100 are disposed to overlap each other when viewed from the forehead 510 side of the worker 500.

This reduces an uncomfortable feeling that the worker 500 has when the worker 500 wears the sensor for the living body (helmet 1). Further, the measuring hole 350 formed in the headband 300 and the light input/output portion 105F formed in the first housing 105 of the first sensor module 100 overlap each other when the forehead 510 of the worker 500 is viewed in a plan view, thereby making it possible for the first sensor module 100 to reliably measure the biological signals of the worker 500.

Referring to FIG. 7, a functional block diagram of the first sensor module 100 and the second sensor module 200 will be described. FIG. 7 is a functional block diagram related to the helmet 1 according to the first embodiment of the present disclosure.

The first sensor module 100 includes the sensor 105E and a control unit 155. The sensor 105E includes, for example, a human body temperature sensor element 1051, a heart rate sensor element 1052, a blood flow sensor element 1053, and an acceleration sensor element 1054.

The second sensor module 200 includes a control unit 201, a power storage unit 202, a sensor 203, and a communication unit 204. The sensor 203 includes, for example, an outside temperature sensor element 2031, a humidity sensor element 2032, and a pressure sensor element 2033. The communication unit 204 performs radio communication with an externally-provided measurement data storage device or the like to transmit data measured by the first sensor module 100 or the second sensor module 200 to the measurement data storage device or the like. The measurement data storage device is a device configured to store the measured data of the worker 500 or the ambient environment of the worker 500, and statistically control the data.

As an example, a case in which the first sensor module 100 measures the body temperature of the worker 500 will be described. The human body temperature sensor element 1051 measures the body temperature of the worker 500 from the forehead 510 of the worker 500. The human body temperature sensor element 1051 outputs the body temperature having been measured (measured body temperature) to the control unit 155.

The control unit 155 outputs the measured body temperature to the control unit 201 of the second sensor module 200 via the wiring 400. The control unit 201 outputs the measured body temperature to the communication unit 204. The communication unit 204 outputs the measured body temperature to the measurement data storage device (not illustrated).

The first sensor module 100 is provided with the heart rate sensor element 1052, so that it is possible to measure the heart rate and a level of stress of the worker. Further, the first sensor module 100 is provided with the blood flow sensor element 1053, so that it is possible to measure the physical condition from the blood flow of the worker 500. Furthermore, by being provided with the acceleration sensor element 1054, it is possible to measure a situation in a case where an impact is generated against the worker 500.

Next, a case in which the second sensor module 200 measures an ambient temperature of the worker 500 will be described. The outside temperature sensor element 2031 measures the ambient temperature (outside temperature) of the worker 500. The outside temperature sensor element 2031 outputs the measured outside temperature to the control unit 201. The control unit 201 outputs the outside temperature to the communication unit 204. The communication unit 204 outputs the measured outside temperature to the measurement data storage device (not illustrated).

Accordingly, it is possible to statistically utilize the information on the worker 500 wearing the helmet 1 or the ambient information of the worker 500.

Note that the first sensor module 100 includes the sensor for measuring a state of the worker 500, that is, the state inside the helmet 1. The second sensor module 200 includes a sensor for measuring a state of an outside of the worker 500, that is, the state outside (near) the helmet 1. Therefore, since it is sufficient for the first sensor module 100 to include the sensor for measuring only the state of the worker 500, it is possible to minimize a configuration of the first sensor module 100.

The power storage unit 202 of the second sensor module 200 can be configured to supply power to the first sensor module 100 through the wiring 400 described above. This makes it possible to further minimize the configuration of the first sensor module 100 and to achieve the miniaturization thereof.

The second sensor module 200 is attached to the side head portion SD of the helmet 1. With this, since the communication unit 204 of the second sensor module 200 is attached to the outside of the helmet 1, it is possible to secure the radio wave intensity for the communication unit 204.

The sensors mounted in the first sensor module 100 and the second sensor module 200 are not limited to those described above, and it is sufficient that the first sensor module 100 has a sensor able to measure the biological signals of the worker 500, and that the second sensor module 200 has a sensor able to measure an outside environment of the worker 500.

By using the configuration described above, it is possible to reduce the uncomfortable feeling and the load due to the presence of the sensor when the worker 500 wears the helmet 1. Further, the measuring hole 350 formed in the headband 300 and the light input/output portion 105F formed in the first housing 105 of the first sensor module 100 overlap each other in a plan view, thereby making it possible for the first sensor module 100 to reliably measure the biological signals of the worker 500. Furthermore, the first sensor module 100 can be attached without necessarily changing a structure of a helmet usually used by a worker. In addition, since the first sensor module 100 is configured to be attachable and detachable, it is possible to attach and detach the first sensor module 100 to and from the helmet with ease.

Second Embodiment

Figure 8A:
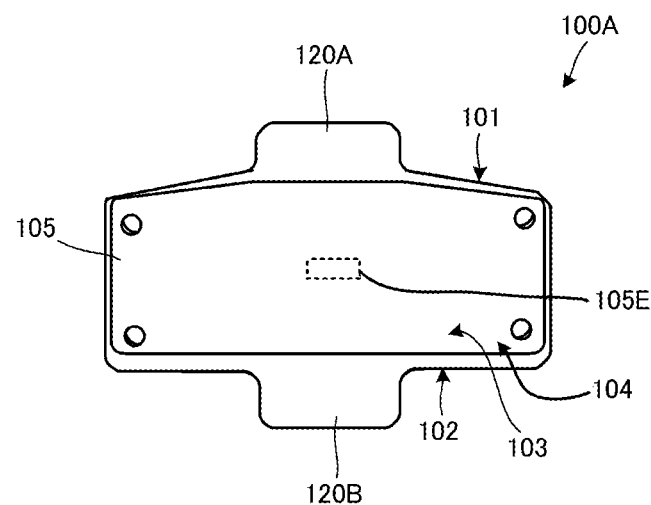
FIG. 8A is a schematic view of a first sensor module 100A according to a second embodiment of the present disclosure.
Figure 8B:
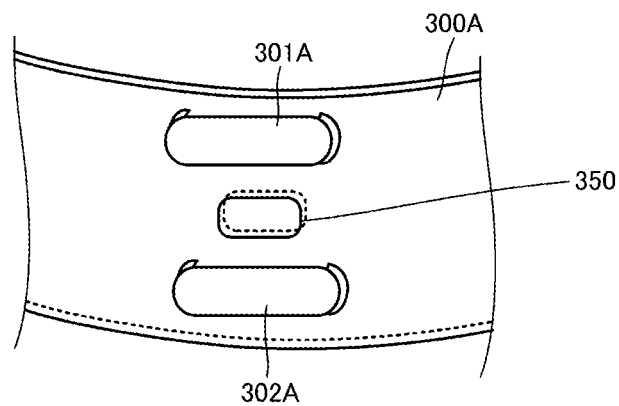
FIG. 8B is an enlarged view illustrating part of a configuration of a headband 300A.
Figure 8C:
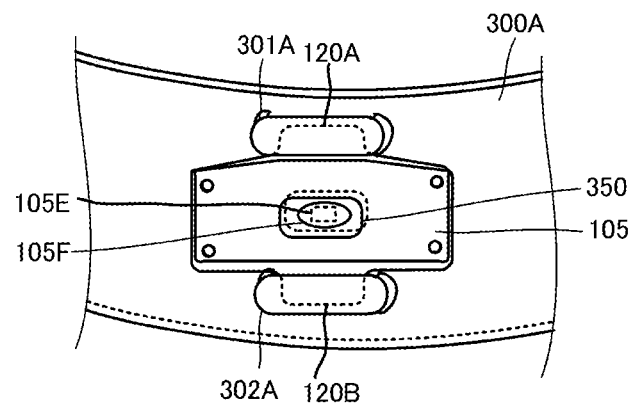
FIG. 8C is a schematic view in which the first sensor module 100A is attached to the headband 300A.

A helmet according to a second embodiment of the present disclosure will be described with reference to the drawings. FIG. 8A is a schematic view of a first sensor module 100A according to a second embodiment of the present disclosure, FIG. 8B is an enlarged view illustrating part of a configuration of a headband 300A, and FIG. 8C is a schematic view in which the first sensor module 100A is attached to the headband 300A. In FIGS. 8A, 8B, and 8C, some components and assignment of some reference signs are omitted in order to make the drawings easy to be seen.

As illustrated in FIGS. 8A, 8B, and 8C, a helmet 1A according to the second embodiment is different from the helmet 1 according to the first embodiment in that a protruding portion 120A and a protruding portion 120B are different in shape, and a projection 301A and a projection 302A are also different in shape. Other configurations of the helmet 1A are similar to those of the helmet 1, and description thereof will be omitted.

As illustrated in FIG. 8A, the first sensor module 100A includes a first housing 105, the protruding portion 120A, and the protruding portion 120B. The first housing 105 includes a first surface 101, a second surface 102, a third surface 103 and a fourth surface 104, and has a substantially rectangular shape in a plan view. The protruding portion 120A is formed on the first surface 101 side of the first housing 105. The protruding portion 120B is formed on the second surface 102 side of the first housing 105. The protruding portion 120A is a "first claw portion" of the present disclosure, and the protruding portion 120B is a "second claw portion" of the present disclosure.

As illustrated in FIG. 8B, the headband 300A includes the projection 301A and the projection 302A. The headband 300A includes the measuring hole 350 between the projection 301A and the projection 302A. The measuring hole 350 is a hole passing through the headband 300A. The projection 301A is a "first projection" of the present disclosure, and the projection 302A is a "second projection" of the present disclosure.

Referring to FIG. 8C, a structure in which the first sensor module 100A (first housing 105) is fixed to the headband 300A will be described.

The protruding portion 120A is inserted into the projection 301A, and the protruding portion 120B is inserted into the projection 302A. In this manner, the first sensor module 100A (first housing 105) is fixed to the headband 300A.

Also, in this configuration, it is possible to reduce the uncomfortable feeling and the load due to the presence of the sensor when the worker 500 wears the helmet 1A. Further, the measuring hole 350 formed in the headband 300A and a light input/output portion 105F formed in the first housing 105 of the first sensor module 100A overlap each other in a plan view, thereby making it possible for the first sensor module 100A to reliably measure the biological signals of the worker 500. Furthermore, the first sensor module 100A can be attached without necessarily changing a structure of a helmet usually used by a worker. In addition, since the first sensor module 100A is configured to be attachable and detachable, it is possible to attach and detach the first sensor module 100A to and from the helmet with ease.

Third Embodiment

Figure 9A:
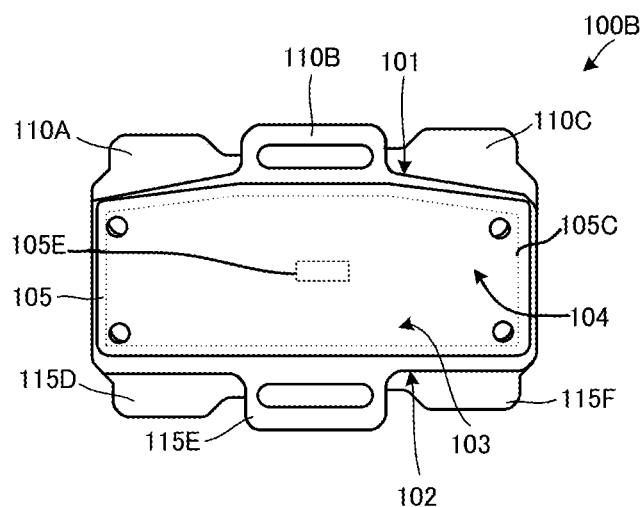
FIG. 9A is a schematic view of a first sensor module 100B according to a third embodiment of the present disclosure.
Figure 9B:
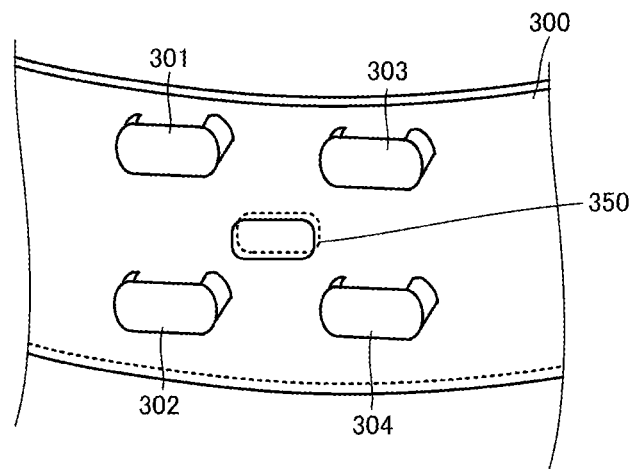
FIG. 9B is an enlarged view illustrating part of a configuration of a headband 300.
Figure 9C:
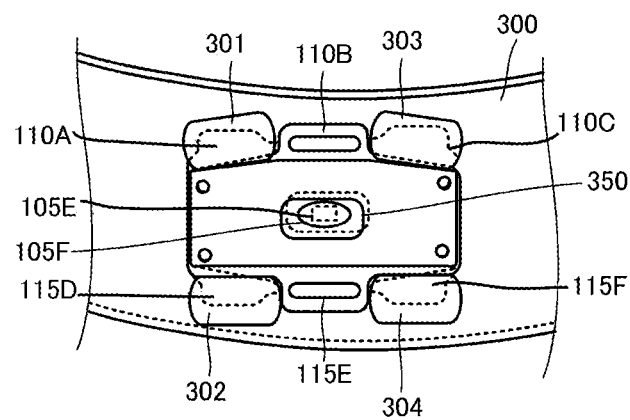
FIG. 9C is a schematic view in which the first sensor module 100B is attached to the headband 300.

A helmet according to a third embodiment of the present disclosure will be described with reference to the drawings. FIG. 9A is a schematic view of a first sensor module 100B according to a third embodiment of the present disclosure, FIG. 9B is an enlarged view illustrating part of a configuration of the headband 300, and FIG. 9C is a schematic view in which the first sensor module 100B is attached to the headband 300. In FIGS. 9A, 9B, and 9C, some components and assignment of some reference signs are omitted in order to make the drawings easy to be seen.

As illustrated in FIGS. 9A, 9B, and 9C, a helmet 1B according to the third embodiment is different from the helmet 1 according to the first embodiment in that a protruding portion 115D, a protruding portion 115E, and a protruding portion 115F are different in shape. Other configurations of the helmet 1B are similar to those of the helmet 1, and description thereof will be omitted.

As illustrated in FIG. 9A, the first sensor module 100B includes the first housing 105, the protruding portion 110A, the protruding portion 110B, the protruding portion 110C, the protruding portion 115D, the protruding portion 115E, and the protruding portion 115F. The first housing 105 includes the first surface 101, the second surface 102, the third surface 103 and a fourth surface 104, and has a substantially rectangular shape in a plan view. The protruding portion 110A, the protruding portion 110B and the projecting portion 110C are formed on the first surface 101 side of the first housing 105 along a longitudinal direction of the first surface 101, and the protruding portion 110B is formed at a position sandwiched between the protruding portion 110A and the protruding portion 110C. The protruding portion 115D, the protruding portion 115E and the projecting portion 115F are formed on the second surface 102 side of the first housing 105 along a longitudinal direction of the second surface 102, and the protruding portion 115E is formed at a position sandwiched between the protruding portion 115D and the protruding portion 115F.

The protruding portion 110A is a "first claw portion" of the present disclosure, the protruding portion 110B is a "fifth claw portion" of the present disclosure, and the protruding portion 110C is a "third claw portion" of the present disclosure. The protruding portion 115D is a "second claw portion" of the present disclosure, the protruding portion 115E is a "sixth claw portion" of the present disclosure, and the protruding portion 115F is a "fourth claw portion" of the present disclosure.

As illustrated in FIG. 9B, the headband 300 has a similar configuration to that of the first embodiment, and includes the projection 301, the projection 302, the projection 303, and the projection 304.

Referring to FIG. 9C, a structure in which the first sensor module 100B (first housing 105) is fixed to the headband 300 will be described.

The protruding portion 110A is inserted into the projection 301, the protruding portion 110C is inserted into the projection 303, the protruding portion 115D is inserted into the projection 302, and the protruding portion 115F is inserted in the projection 304. In this manner, the first sensor module 100B (first housing 105) is fixed to the headband 300.

Since the protruding portion 110B is disposed so as to be sandwiched between the projection 301 and the projection 303, and the protruding portion 115E is disposed so as to be sandwiched between the projection 302 and the projection 304, the first sensor module 100B (first housing 105) can be more reliably fixed to the headband 300.

Also, in this configuration, it is possible to reduce the uncomfortable feeling and the load due to the presence of the sensor when the worker 500 wears the helmet 1B. Further, the measuring hole 350 formed in the headband 300 and a light input/output portion 105F formed in the first housing 105 of the first sensor module 100B overlap each other in a plan view, thereby making it possible for the first sensor module 100B to reliably measure the biological signals of the worker 500. Furthermore, the first sensor module 100B can be attached without necessarily changing the structure of the helmet usually used by the worker. In addition, since the first sensor module 100B is configured to be attachable and detachable, it is possible to attach and detach the first sensor module 100B to and from the helmet with ease.

Fourth Embodiment

Figure 10:
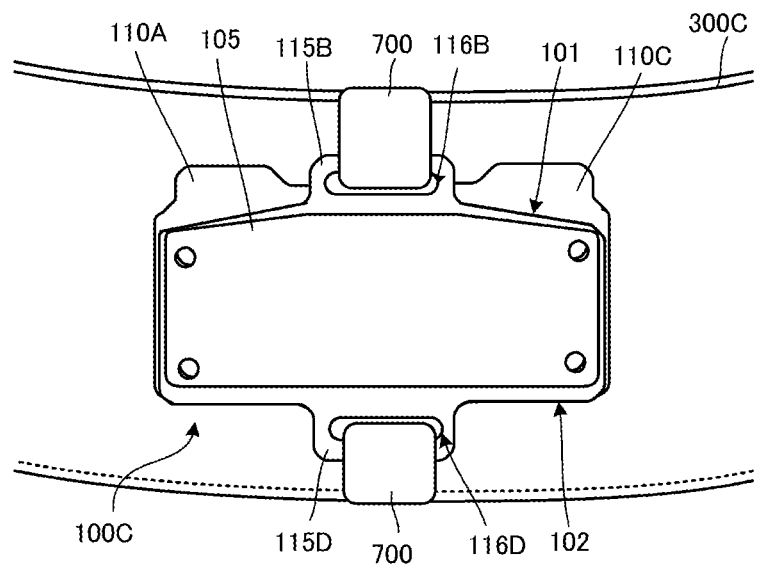
FIG. 10 is a schematic view of a first sensor module 100C according to a fourth embodiment of the present disclosure.

A helmet according to a fourth embodiment of the present disclosure will be described with reference to the drawings. FIG. 10 is a schematic view of a first sensor module 100C according to the fourth embodiment of the present disclosure. In FIG. 10, some components and assignment of some reference signs are omitted in order to make the drawing easy to be seen.

As illustrated in FIG. 10, a helmet 1C according to the fourth embodiment is different from the helmet 1 according to the first embodiment in that the shapes of the protruding portion 115B and the protruding portion 115D, and a structure of fixing to a headband 300C are different. Other configurations of the helmet 1C are similar to those of the helmet 1, and description thereof will be omitted.

As illustrated in FIG. 10, the first sensor module 100C includes the first housing 105, the protruding portion 110A, the protruding portion 115B, a protruding portion 110C, and the protruding portion 115D. The protruding portion 115B is a "first claw portion" of the present disclosure, and the protruding portion 115D is a "second claw portion" of the present disclosure.

A first fixing hole 116B is formed in the protruding portion 115B. A second fixing hole 116D is formed in the protruding portion 115D.

A fixing band 700 is set passing through the first fixing hole 116B and the second fixing hole 116D, and the first sensor module 100C (first housing 105) is fixed to the headband 300C by using the fixing band 700.

Also, in this configuration, it is possible to reduce the uncomfortable feeling and the load due to the presence of the sensor when the worker 500 wears the helmet 1C. The first sensor module 100C is able to reliably measure the biological signals of the worker 500. Further, the first sensor module 100C can be attached without necessarily changing the structure of the helmet usually used by the worker. In addition, since the first sensor module 100C is configured to be attachable and detachable, it is possible to attach and detach the first sensor module 100C to and from a helmet with ease.

Even in a case where the projection 301, the projection 302, the projection 303, and the projection 304 are not formed in the headband 300C, it is possible to fix the first sensor module 100C to the headband 300C with ease.

Fifth Embodiment

Figure 11:
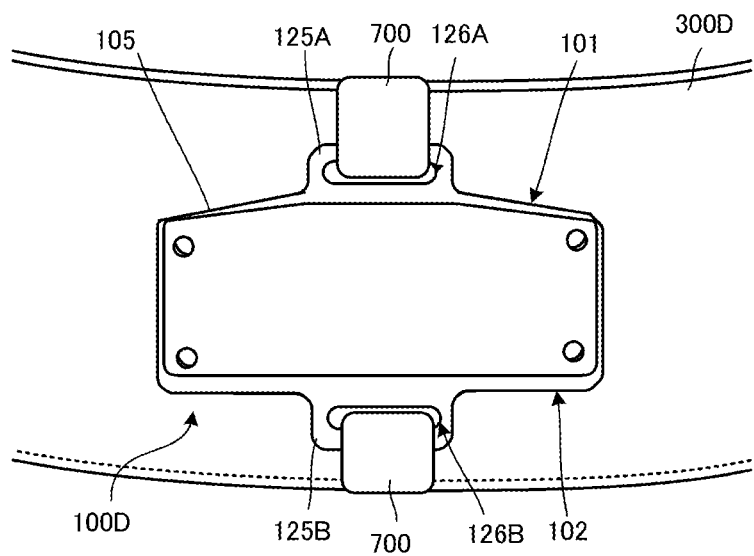
FIG. 11 is a schematic view of a first sensor module 100D according to a fifth embodiment of the present disclosure.

A helmet according to a fifth embodiment of the present disclosure will be described with reference to the drawings. FIG. 11 is a schematic view of a first sensor module 100D according to the fifth embodiment of the present disclosure. In FIG. 11, some components and assignment of some reference signs are omitted in order to make the drawing easy to be seen.

As illustrated in FIG. 11, a helmet 1D according to the fifth embodiment is different from the helmet 1A according to the second embodiment in that shapes of a protruding portion 125A and a protruding portion 125B, and a structure of fixing to a headband 300D are different. Other configurations of the helmet 1D are similar to those of the helmet 1A, and description thereof will be omitted.

As illustrated in FIG. 11, the first sensor module 100D includes the first housing 105, the protruding portion 125A, and the protruding portion 125B. The protruding portion 125A is a "first claw portion" of the present disclosure, and the protruding portion 125B is a "second claw portion" of the present disclosure.

A first fixing hole 126A is formed in the protruding portion 125A. A second fixing hole 126B is formed in the protruding portion 125B.

The fixing band 700 is set passing through the first fixing hole 126A and the second fixing hole 126B, and the first sensor module 100D (first housing 105) is fixed to the headband 300D by using the fixing band 700.

Also, in this configuration, it is possible to reduce the uncomfortable feeling and the load due to the presence of the sensor when the worker 500 wears the helmet 1D. The first sensor module 100D is able to reliably measure the biological signals of the worker 500. Further, the first sensor module 100D can be attached without necessarily changing a structure of a helmet usually used by a worker. In addition, since the first sensor module 100D is configured to be attachable and detachable, it is possible to attach and detach the first sensor module 100D to and from the helmet with ease.

Even in a case where the projection 301 and the projection 302 are not formed in the headband 300D, it is possible to fix the first sensor module 100D to the headband 300D with ease.

Sixth Embodiment

Figure 12:
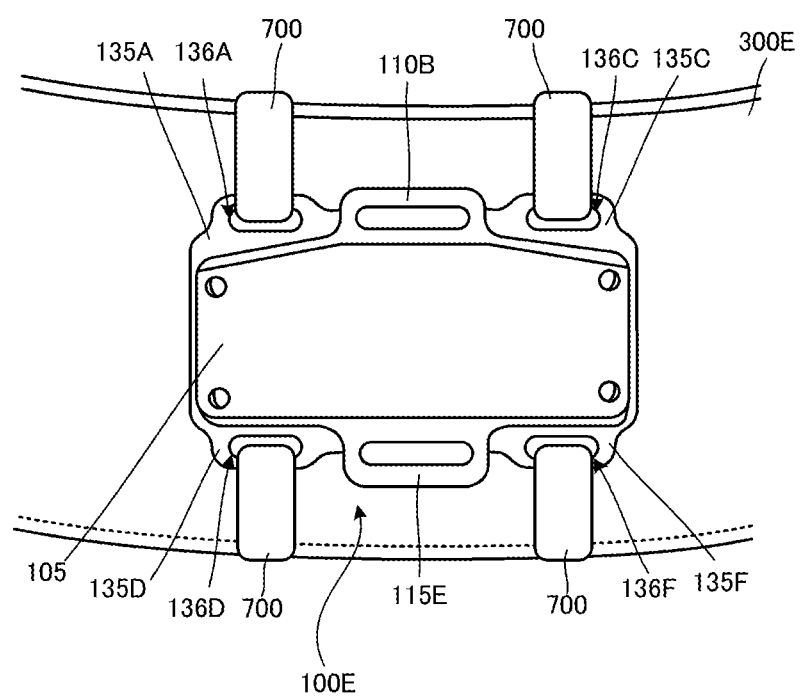
FIG. 12 is a schematic view of a first sensor module 100E according to a sixth embodiment of the present disclosure.

A helmet according to a sixth embodiment of the present disclosure will be described with reference to the drawings. FIG. 12 is a schematic view of a first sensor module 100E according to the sixth embodiment of the present disclosure. In FIG. 12, some components and assignment of some reference signs are omitted in order to make the drawing easy to be seen.

As illustrated in FIG. 12, a helmet 1E according to the sixth embodiment is different from the helmet 1B according to the third embodiment in that shapes of a protruding portion 135A, a protruding portion 135C, a protruding portion 135D and a protruding portion 135F, and a structure of fixing to a headband 300E are different. Other configurations of the helmet 1E are similar to those of the helmet 1B, and description thereof will be omitted.

As illustrated in FIG. 12, the first sensor module 100E includes the protruding portion 135A, the protruding portion 110B, the protruding portion 135C, the protruding portion 135D, the protruding portion 115E, and the protruding portion 135F. The protruding portion 135A is a "first claw portion" of the present disclosure, the protruding portion 110B is a "fifth claw portion" of the present disclosure, and the protruding portion 135C is a "third claw portion" of the present disclosure. The protruding portion 135D is a "second claw portion" of the present disclosure, the protruding portion 115E is a "sixth claw portion" of the present disclosure, and the protruding portion 135F is a "fourth claw portion" of the present disclosure.

A first fixing hole 136A is formed in the protruding portion 135A, and a second fixing hole 136D is formed in the protruding portion 135D. A third fixing hole 136C is formed in the protruding portion 135C, and a fourth fixing hole 136F is formed in the protruding portion 135F.

The fixing band 700 is set passing through the first fixing hole 136A, the second fixing hole 136D, the third fixing hole 136C and the fourth fixing hole 136F, and the first sensor module 100E (first housing 105) is fixed to the headband 300E by using the fixing band 700.

Also, in this configuration, it is possible to reduce the uncomfortable feeling and the load due to the presence of the sensor when the worker 500 wears the helmet 1E. The first sensor module 100E is able to reliably measure the biological signals of the worker 500. Further, the first sensor module 100E can be attached without necessarily changing a structure of a helmet usually used by a worker. In addition, since the first sensor module 100E is configured to be attachable and detachable, it is possible to attach and detach the first sensor module 100E to and from the helmet with ease.

Even in a case where the projection 301, the projection 302, the projection 303, and the projection 304 are not formed in the headband 300E, it is possible to fix the first sensor module 100E to the headband 300E with ease.

The embodiments are not limited to the configurations of the embodiments described above, and the combination of these embodiments may be changed to configure another embodiment.

REFERENCE SIGNS LIST

FD FRONT HEAD PORTION
SD SIDE HEAD PORTION
1, 1A, 1B, 1C, 1D, 1E HELMET
10 CAP BODY
100, 100A, 100B, 100C, 100D, 100E FIRST SENSOR MODULE
101 FIRST SURFACE
102 SECOND SURFACE
103 THIRD SURFACE
104 FOURTH SURFACE
105 FIRST HOUSING
105A LID PORTION
105B ADHESIVE TAPE
105C SUBSTRATE
105D BODY PORTION
105E SENSOR
105F LIGHT INPUT/OUTPUT PORTION
110A, 110B, 110C, 110D, 115B, 115D, 115E, 115F, 120A, 120B, 125A, 125B, 135A, 135C, 135D, 135F PROTRUDING PORTION
116B, 126A, 136A FIRST FIXING HOLE
116D, 126B, 136D SECOND FIXING HOLE
136C THIRD FIXING HOLE
136F FOURTH FIXING HOLE
155 CONTROL UNIT
200 SECOND SENSOR MODULE
201 CONTROL UNIT
202 POWER STORAGE UNIT
203 SENSOR
204 COMMUNICATION UNIT
300, 300A, 300C, 300D, 300E HEADBAND
301, 301A, 302, 302A, 303, 304 PROJECTION
305 ATTACHMENT UNIT
350 MEASURING HOLE
400 WIRING
500 WORKER
510 FOREHEAD
700 FIXING BAND
1051 HUMAN BODY TEMPERATURE SENSOR ELEMENT
1052 HEART RATE SENSOR ELEMENT
1053 BLOOD FLOW SENSOR ELEMENT
1054 ACCELERATION SENSOR ELEMENT
2031 OUTSIDE TEMPERATURE SENSOR ELEMENT
2032 HUMIDITY SENSOR ELEMENT
2033 PRESSURE SENSOR ELEMENT

The invention claimed is:

1. A helmet comprising:
a non-contact sensor for a living body;
a cap body; and
a headband attached to an inner side of the cap body,
wherein the headband comprises a first projection and a second projection on a surface facing a front head portion of the cap body,
the non-contact sensor for the living body includes a first housing having a first surface and a second surface opposing the first surface, a first claw portion provided on the first surface, and a second claw portion provided on the second surface, and
the first claw portion is in contact with and fixed to the first projection, and the second claw portion is contact with and fixed to the second projection.

2. The helmet according to claim 1,
wherein the non-contact sensor for the living body further includes a third claw portion provided on the first surface and a fourth claw portion provided on the second surface,
the headband includes a third projection and a fourth projection,
the first claw portion is inserted into and fixed to the first projection,
the second claw portion is inserted into and fixed to the second projection,
the third claw portion is inserted into and fixed to the third projection, and
the fourth claw portion is inserted into and fixed to the fourth projection.

3. The helmet according to claim 2,
wherein the non-contact sensor for the living body further includes a fifth claw portion having a first fixing hole and provided between the first claw portion and the third claw portion on the first surface, and a sixth claw portion having a second fixing hole and provided between the second claw portion and the fourth claw portion on the second surface.

4. The helmet according to claim 3, further comprising:
a second housing on an outer side portion of the cap body; and
a power storage unit, a radio communication unit, and an environmental sensor each housed in the second housing,
wherein the first housing and the second housing are connected to each other by wiring between an inner side of the cap body and the headband.

5. The helmet according to claim 3,
wherein the first housing includes the first surface, the second surface, a body portion, and a lid portion, and
the first surface, the second surface and the body portion, or the first surface, the second surface and the lid portion are bonded to one another by a double-sided tape.

6. The helmet according to claim 2, further comprising:
a second housing on an outer side portion of the cap body; and
a power storage unit, a radio communication unit, and an environmental sensor each housed in the second housing,
wherein the first housing and the second housing are connected to each other by wiring between an inner side of the cap body and the headband.

7. The helmet according to claim 2,
wherein the first housing includes the first surface, the second surface, a body portion, and a lid portion, and the first surface, the second surface and the body portion, or the first surface, the second surface and the lid portion are bonded to one another by a double-sided tape.

8. The helmet according to claim 1,
wherein the non-contact sensor for the living body further includes a third claw portion provided on the first surface,
the headband includes a third projection and a fourth projection,
the first claw portion is inserted into and fixed to the first projection,
the third claw portion is inserted into and fixed to the third projection, and
the second claw portion is sandwiched between the second projection and the fourth projection.

9. The helmet according to claim 8, further comprising:
a second housing on an outer side portion of the cap body; and
a power storage unit, a radio communication unit, and an environmental sensor each housed in the second housing,
wherein the first housing and the second housing are connected to each other by wiring between an inner side of the cap body and the headband.

10. The helmet according to claim 8,
wherein the first housing includes the first surface, the second surface, a body portion, and a lid portion, and
the first surface, the second surface and the body portion, or the first surface, the second surface and the lid portion are bonded to one another by a double-sided tape.

11. The helmet according to claim 1,
wherein a first fixing hole and a second fixing hole are in the first claw portion and the second claw portion respectively.

12. The helmet according to claim 11, further comprising:
a second housing on an outer side portion of the cap body; and
a power storage unit, a radio communication unit, and an environmental sensor each housed in the second housing,
wherein the first housing and the second housing are connected to each other by wiring between an inner side of the cap body and the headband.

13. The helmet according to claim 11,
wherein the first housing includes the first surface, the second surface, a body portion, and a lid portion, and
the first surface, the second surface and the body portion, or the first surface, the second surface and the lid portion are bonded to one another by a double-sided tape.

14. The helmet according to claim 1, further comprising:
a second housing on an outer side portion of the cap body; and
a power storage unit, a radio communication unit, and an environmental sensor each housed in the second housing,
wherein the first housing and the second housing are connected to each other by wiring between an inner side of the cap body and the headband.

15. The helmet according to claim 14,
wherein the first housing includes the first surface, the second surface, a body portion, and a lid portion, and the first surface, the second surface and the body portion, or the first surface, the second surface and the lid portion are bonded to one another by a double-sided tape.

16. The helmet according to claim 1,
wherein the first housing includes the first surface, the second surface, a body portion, and a lid portion, and
the first surface, the second surface and the body portion, or the first surface, the second surface and the lid portion are bonded to one another by a double-sided tape.

17. The helmet according to claim 1,
wherein the non-contact sensor for the living body includes a sensor element with an optical system,
the headband includes a measuring hole, and
the measuring hole and a light input/output portion of the sensor element face each other.

18. The helmet according to claim 1,
wherein a first fixing hole and a second fixing hole are in the first claw portion and the second claw portion respectively.

\* \* \* \* \*